United States Patent
Scherr et al.

(10) Patent No.: US 6,867,336 B2
(45) Date of Patent: Mar. 15, 2005

(54) METHOD FOR THE CONTINUOUS PRODUCTION OF 2-BROMO-2-NITRO-1,3-PROPANEDIOL

(75) Inventors: Günter Scherr, Ludwigshafen (DE); Thomas Bogenstätter, Bad Dürkheim (DE); Jürgen Huff, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/485,207

(22) PCT Filed: Aug. 1, 2002

(86) PCT No.: PCT/EP02/08595

§ 371 (c)(1),
(2), (4) Date: Jan. 29, 2004

(87) PCT Pub. No.: WO03/011811

PCT Pub. Date: Feb. 13, 2003

(65) Prior Publication Data

US 2004/0186326 A1 Sep. 23, 2004

(30) Foreign Application Priority Data

Aug. 2, 2001 (DE) ......................... 101 37 829

(51) Int. Cl.$^7$ .......................... C07C 31/34; C07C 31/36
(52) U.S. Cl. ...................... 568/846; 568/841; 568/844; 568/845
(58) Field of Search ................. 568/846, 841, 568/844, 845

(56) References Cited

U.S. PATENT DOCUMENTS

| | | |
|---|---|---|
| 3,534,112 A | 10/1970 | Tindall |
| 3,658,921 A | 4/1972 | Wessendorf |
| 3,711,561 A | 1/1973 | Wessendorf |
| 5,001,285 A | 3/1991 | Wuest et al. |
| 5,041,691 A | 8/1991 | Wuest et al. |

OTHER PUBLICATIONS

Rec. Tra. Chim. Pays Bas, Den Otter, vol. 57, 1938, 13–24.

*Primary Examiner*—Elvis O. Price
(74) *Attorney, Agent, or Firm*—Keil & Weinkauf

(57) ABSTRACT

In a process for the continuous preparation of 2-bromo-2-nitro-1,3-propanediol, nitromethane is firstly reacted with formaldehyde and alkali metal hydroxide and the reaction mixture obtained in this way is subsequently reacted with bromine.

14 Claims, 2 Drawing Sheets

METHOD FOR THE CONTINUOUS PRODUCTION OF 2-BROMO-2-NITRO-1,3-PROPANEDIOL

Figure 1:
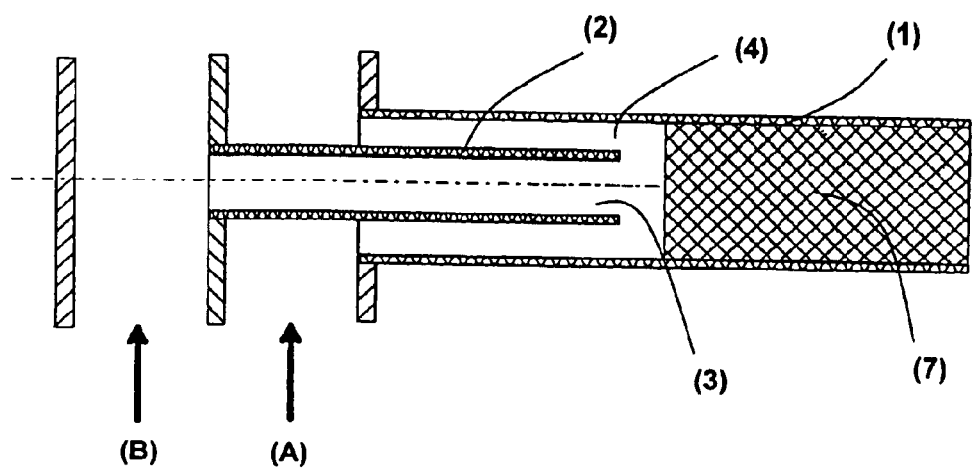

The present invention relates to a process for the continuous preparation. of 2-bromo-2-nitro-1,3-propanediol, in which nitromethane is firstly reacted with formaldehyde and alkali metal hydroxide and the reaction mixture obtained in this way is subsequently reacted with bromine.

2-Bromo-2-nitro-1,3-propanediol, referred to as bronopol for short, is an economically very important biocide which is used as a disinfectant and preservative in pharmaceuticals, toiletries, cosmetics and household products.

2-Bromo-2-nitro-1,3-propanediol is usually prepared by bishydroxymethylation of nitromethane using formaldehyde in the presence of a base, which gives the salt corresponding to 2-nitropropane-1,3-diol and this is subsequently reacted with bromine to form 2-bromo-2-nitropropane-1,3-diol (see scheme 1).

Scheme 1:

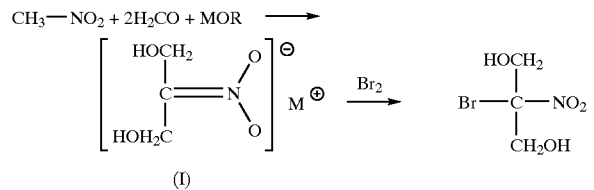

M=one cation equivalent, e.g. Na, K, 1/2 Ca
R=H, alkyl

The first reaction step shown in scheme 1 is usually carried out in an aqueous or aqueous/alcohol solvent using an alkali metal hydroxide or an alkali metal alkoxide to give a solution of the salt of 2-nitropropane-1,3-diol shown in scheme 1, and this solution is subsequently added to a solution of bromine, as described, for example, by Den Otter in Rec. Trav. Chim. Pays Bas, volume 57, 1938, pages 13–24.

A major problem is that 2-bromo-2-nitropropane-1,3-diol tends to decompose in an alkaline medium. In addition, both reaction steps are strongly exothermic. It is therefore important that the reaction be carried out in a controlled manner. For this reason, the processes of the prior art are customarily carried out using only dilute solutions.

Owing to the strongly exothermic nature of the reaction steps, it has hitherto been considered that a continuous process for preparing 2-bromo-2-nitro-1,3-propanediol would not be controllable. For this reason, 2-bromo-2-nitro-1,3-propanediol has hitherto been prepared only by batch processes since these allow the reaction to be carried out in a controlled manner.

It has surprisingly been found that 2-bromo-2-nitro-1,3-propanediol can nevertheless be prepared continuously if nitromethane together with an aqueous formaldehyde solution and an aqueous alkali metal hydroxide solution are fed in about the required stoichiometry with mixing of these liquids into a first reaction zone, the reaction solution is taken continuously from this reaction zone and fed directly, i.e. without isolation of the reaction solution, together with bromine with mixing of reaction solution and bromine into a second cooled reaction zone and 2-bromo-2-nitro-1,3-propanediol is isolated from the aqueous reaction mixture obtained.

The present invention accordingly provides a process for the continuous preparation of 2-bromo-2-nitro-1,3-propanediol, which comprises i) feeding nitromethane and one or two aqueous solutions comprising formaldehyde and alkali metal hydroxide continuously with mixing into a first, cooled reaction zone at molar ratios of formaldehyde to nitromethane of 1.9–2.2:1 and of alkali metal hydroxide to nitromethane of from 0.95:1 to 1.1:1, ii) taking the aqueous reaction mixture obtained in i) continuously from the first reaction zone and directly afterwards feeding this continuously with mixing together with bromine into at least one second, cooled reaction zone, and iii) isolating 2-bromo-2-nitro-1,3-propanediol from the aqueous reaction mixture obtained in ii).

For the purposes of the present invention, aqueous solutions or aqueous reaction mixtures are solutions/mixtures in which the solvent is water or a mixture of water and water-miscible inert organic solvents, with water being the main constituent, i.e. making up at least 50% by volume, preferably at least 80% by volume and in particular at least 95% by volume, of the water/solvent mixture. Suitable water-miscible, inert solvents are $C_1$–$C_4$-alcohols such as methanol, ethanol, n-propanol, isopropanol, n-butanol and tert-butanol. In a preferred embodiment, water is used as solvent.

In the process of the present invention, it is important that intensive mixing of the reactants is effected in the cooled reaction zone in the first stage i) of the preparation of 2-bromo-2-nitro-1,3-propanediol. Intensive mixing is also important in the second stage ii). Mixing is preferably effected by feeding the liquid reactants into the first and preferably also the second reaction stage via apparatuses which are suitable for the continuous mixing of liquids. In the case of relatively small apparatus dimensions, mixing of the reactants can also be achieved by introducing the liquid reactants into the reactor with swirling of the liquid streams, for example via two inlets for the liquid streams which are in the direct vicinity of one another. This procedure has been found to be particularly useful in laboratory apparatuses and miniplants having reactor volumes (volumes of the respective reaction zone) of $\leq 1000$ ml, preferably $\leq 200$ ml.

The apparatuses for the continuous mixing of liquids (mixing elements) can be, depending on the reactor geometry, either jet mixers, static mixers or dynamic mixers. Such mixers are known to those skilled in the art, e.g. from H.-J. Henzler, "Continuous Mixing of Fluids" in Ullmann's Encyclopedia of Industrial Chemistry, 5th ed. on CD-ROM, WILEY-VCH, 1997, Weinheim. Preference is given to using static mixers, namely mixers having stationary internals, particularly in the case of tubular reactor geometries. The static mixers can have an arrangement of a plurality of deflection or impingement plates, mesh-like internals, e.g. Koax mixers or the Sulzer types SMX, SMV, SMR, SMF or SMXL, or helical internals as in the case of Kenics, Fix-Mix, Lightning or Helax mixers, or combinations of various types of static mixer.

It has been found to be advantageous for the geometry of the reaction zone to be such that turbulent flow conditions prevail in it. Here, the use of tubular reactors, e.g. tube reactors or shell-and-tube reactors, has been found to be particularly useful. In addition, these reactor shapes allow the enlarged quantity of heat of reaction to be removed readily. The reaction tubes can have either circular or ellipsoidal cross sections. The dimensions of the reactor are generally such that the ratio of the length of the reaction tube to the diameter is in the range from 100:1 to 1000000:1, preferably in the range from 100:1 to 10000:1 and in particular in the range from 250:1 to 1000:1. In the case of an ellipsoidal cross section of the reaction tube, the tube diameter is the mean of the major and minor axes. The tubes of the reactor can have a straight geometry, but they can also have one or more curved tube segments, for example tube segments having a plurality of successive curves having an alternating direction of curvature. The latter reactors are known, for example, from WO 98/08602, whose disclosure is hereby incorporated by reference.

According to the present invention, the reaction zones are cooled, i.e. they are equipped with cooling facilities. In principle, all types of external cooling using cooling liquids, e.g. jacket cooling, cooling coils located on the walls of the reactors or cooling baths, are suitable here. It is particularly advantageous for the reactors to be configured in the form of shell-and-tube heat exchangers, i.e. in the form of bundles of tubes around which the liquid cooling medium is passed. Suitable cooling media are in principle all known cooling media, in particular cooled brines or liquid ammonia.

According to the present invention the tubular reactors have at least one mixing element in the immediate vicinity of the inlets for the liquid reactants. Of course, the tubular reactors can also have further mixers, in particular static mixers, at other points along the reaction tubes.

In the process of the present invention, the alkali metal hydroxide and the formaldehyde can be fed into the reaction zone either as an aqueous solution comprising the two components or as separate aqueous solutions. The nitromethane can be fed into the reaction zone at any point, but can also be fed in at a plurality of points. The nitromethane is always fed in via an apparatus suitable for mixing liquids. In this way, intensive mixing of the nitromethane with the aqueous solutions of the other reactants or with the reaction mixture present in the reaction zone is ensured.

The introduction of at least part of the nitromethane and of the other liquid reactants is preferably carried out via two or three inlets located in the immediate vicinity of one another and in the immediate vicinity of at least one mixing element. In the case of the tubular reactor geometries which are preferred according to the present invention, these two or three inlets are located at one end of the reaction tube. At least one apparatus suitable for mixing liquids is also located at this end.

In a preferred embodiment of this arrangement, the inlet provided for the nitromethane and the inlet provided for the formaldehyde and alkali metal hydroxide together form a nozzle having a central outlet and a second outlet arranged concentrically around this central outlet. The shape of these outlets is of minor importance and they can have circular or annular cross sections or ellipsoidal cross sections. The outlet orifices of this nozzle preferably have dimensions such that the ratio of their cross-sectional areas corresponds approximately to that of the mass flows to be delivered through them. In this arrangement, preference is given to feeding in the nitromethane through the central outlet orifice and feeding in the aqueous solution comprising formaldehyde and alkali metal hydroxide through the outlet orifice arranged concentrically around the central opening via the mixing element of the reaction zone. This arrangement is particularly preferred in the case of the tubular reactor geometry which is preferred according to the present invention.

A particularly preferred embodiment of this specific arrangement is shown for a tubular reaction space in FIG. 1.

Alkali metal hydroxides suitable for the process of the present invention are, in particular, sodium hydroxide and potassium hydroxide. Particular preference is given to using sodium hydroxide.

If alkali metal hydroxide and formaldehyde are fed in as separate aqueous solutions, the concentration of alkali metal hydroxide and of formaldehyde in these aqueous solutions is in each case preferably in the range from 10 to 50% by weight, in particular in the range from 15 to 30% by weight, in each case based on the total weight of the solution. If these components are introduced via a common solution, the total concentration of formaldehyde and alkali metal hydroxide is preferably from 10 to 50% by weight, in particular from 15 to 30% by weight, based on the total weight of the solution. Nitromethane is preferably introduced as such into the first reaction zone.

The concentrations of formaldehyde and alkali metal hydroxide are preferably selected so that, corresponding to the molar ratio of nitromethane, formaldehyde and alkali metal hydroxide set, the concentration of nitromethane or its reaction product in the reaction mixture of the first reaction stage is in the range from 1 to 10 mol/l, in particular in the range from 1.2 mol/l to 5 mol/l and particularly preferably in the range from 1.5 mol/l to 4 mol/l. Correspondingly, the proportion of nitromethane in the total of the streams fed in is preferably from about 60 g/l to 600 g/l, in particular from 7.5 g/l to 300 g/l and particularly preferably from 90 g/l to 250 g/l or from 5.3% by volume to 53% by volume, in particular from 6.6% by volume to 26.5% by volume and particularly preferably from 8.0% by volume to 22.1% by volume, based on the total volume of the streams.

According to the present invention, the reactants are introduced into the first reaction stage in approximately the amount required according to the stoichiometry indicated at the outset, with an up to 10% excess of alkali metal hydroxide and formaldehyde, based on nitromethane, or a small deficiency of these components being possible. For the purposes of the present invention, stated stochiometries of the reactants are on a molar basis. However, preference is given to using formaldehyde and alkali metal hydroxide in an at least equimolar amount, based on nitromethane, and preferably in a small excess of preferably from 0.5 to 10 mol %, in particular from 2 to 7.5 mol %. Accordingly, the molar ratio of formaldehyde to nitromethane is preferably in the range from 2.01:1 to 2.2:1, in particular in the range from 2.05:1 to 2.15:1, and the molar ratio of alkali metal hydroxide to nitromethane is in the range from 1.01:1 to 1.1:1, in particular in the range from 1.02:1 to 1.07:1.

The reaction temperature in the first reaction zone is preferably kept below 40° C. by cooling of the reaction zone. In particular, the reaction in the first reaction zone is carried out at from 10 to 40° C., particularly preferably from 15 to 30° C. and especially from 20 to 25° C.

In the present process, it has been found to be advantageous for the residence time of the reactants in the first reaction zone to be very low, preferably not more than 3 minutes, e.g. from 5 seconds to 3 minutes, in particular from 10 seconds to 1 minute, particularly preferably from 10 seconds to 45 seconds and very particularly preferably from 10 seconds to 30 seconds.

The solution of the alkali metal salt of 2-nitropropane-1,3-diol obtained in the first reaction zone is then immediately, i.e. without intermediate storage, fed directly to the second reaction stage. According to the present invention, it is preferably fed in together with bromine via at least one apparatus suitable for mixing liquids. Here too, preference is given to static mixers. The aqueous, 2-bromo-2-nitropropane-1,3-diol-containing reaction mixture is naturally taken continuously from the second reaction zone, or in the case of a plurality of reaction zones from the last reaction zone, and the desired product is isolated therefrom.

The second reaction zone likewise preferably has a tubular geometry. Accordingly, the second reaction zone is likewise preferably configured as a tube reactor or as a shell-and-tube reactor.

Figure 1A:
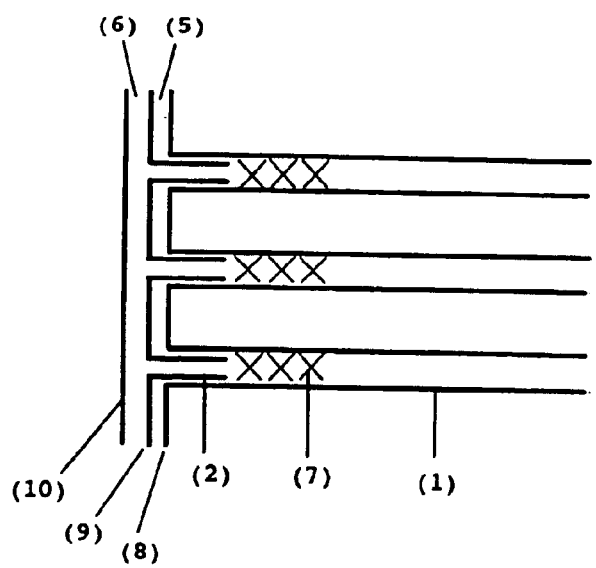

The aqueous reaction mixture obtained in reaction stage i) and bromine are preferably added via two inlet points located in the vicinity of one another and in the direct vicinity of the mixing element. Here too, preference is given to an arrangement in which the bromine and the aqueous reaction solution from stage i) are fed into the reaction zone, preferably the reaction tube, via a nozzle having a first central outlet and a second outlet arranged concentrically around the central outlet via an apparatus suitable for mixing liquids. In particular, an arrangement as is explained in detail for the introduction of the reactants into stage i) and shown, for example, in FIGS. 1 and 1a is used. In such arrangements, the bromine is preferably added via the central outlet and the aqueous reaction solution is added via the second, annular outlet around the central outlet.

The amount of bromine which is fed into the second stage corresponds substantially to the stoichiometry required, with bromine also being able to be used in a small excess or deficiency which generally does not exceed 20 mol %. To calculate the stoichiometry, the amount of nitromethane used is employed as a basis. It has been found to be advantageous to use bromine in not more than the equimolar amount, based on nitromethane used, and in particular in a small deficiency. The molar ratio of bromine to the nitromethane used in the first stage is therefore preferably from 1.8:1 to 1.99:1, in particular from 1.9:1 to 1.95:1.

The temperature of the reaction mixture in the second reaction zone is preferably kept below 40° C., e.g. in the range from 5 to 40° C., in particular in the range from 10 to 30° C. and particularly preferably in the range from 15 to 25° C., by intensive cooling. The residence time of the reactants in the second reaction zone preferably does not exceed 3 minutes and is preferably from 10 seconds to 3 minutes, in particular from 10 seconds to 2 minutes and particularly preferably from 15 seconds to 1 minute.

The aqueous reaction mixture leaving the second reaction zone is generally in the form of an aqueous solution of 2-bromo-2-nitro-1,3-propanediol and alkali metal bromide. To isolate the 2-bromo-2-nitro-1,3-propanediol, the reaction mixture obtained is cooled, preferably to below 5° C., in particular below 0° C., with the lower temperature limit being imposed by the freezing point of the aqueous reaction mixture. The mixture is preferably cooled to a temperature in the range from −10 to −2° C. The 2-bromo-2-nitro-1,3-propanediol present in the reaction solution crystallizes out virtually completely under these conditions and can be filtered off by customary methods. For further purification, the 2-bromo-2-nitro-1,3-propanediol is preferably washed with small amounts of water and organic solvents. Subsequent drying then gives the 2-bromo-2-nitro-1,3-propanediol in a form which is sufficiently pure for most applications. Further purification of the 2-bromo-2-nitro-1,3-propanediol can be carried out by recrystallization, e.g. from water, alcohols, e.g. $C_1$–$C_4$-alcohols such as methanol, ethanol, n-propanol and isopropanol, ethers such as diethyl ether, diisopropyl ether and methyl tert-butyl ether, chlorinated solvents and the like. Further 2-bromo-2-nitro-1,3-propanediol can be obtained by evaporating the reaction solution and repeating the crystallization and/or by salting out, preferably by means of alkali metal bromide or chloride, e.g. NaBr or NaCl.

Surprisingly, the process of the present invention gives 2-bromo-2-nitro-1,3-propanediol in a significantly higher yield, based on nitromethane used, than the batchwise processes of the prior art. Thus, the selectivity based on nitromethane used is usually above 90%, in particular in the range from 95 to 99%. The yield of 2-bromo-2-nitro-1,3-propanediol, based on nitromethane used, is generally above 80% of the theoretical yield and is frequently at least 85%. Accordingly, the formation of by-products is lower. The process of the present invention is also more economical since it is not necessary to employ very dilute solutions as have to be used in the batchwise processes. In addition, the space-time yield in the process of the present invention is very much higher, generally by a factor of at least 100, in particular at least 200, than in the batch processes of the prior art, so that a given amount of desired product can be produced in very much smaller reactor volumes than would be necessary for the batch processes. This improves the economics, since smaller amounts of material are necessary for the construction of plants. In addition, the process of the present invention can be controlled very precisely. Use of organic solvents as are, according to the literature, required in the processes of the prior art is not necessary in the process of the present invention.

The figures and the examples below illustrate the invention without restricting its scope.

FIG. 1: Diagram of a preferred arrangement for introducing the reactants into a reaction tube.

FIG. 1a: Schematic diagram of a plurality of assemblies as per FIG. 1 connected to one another.

Figure 2:
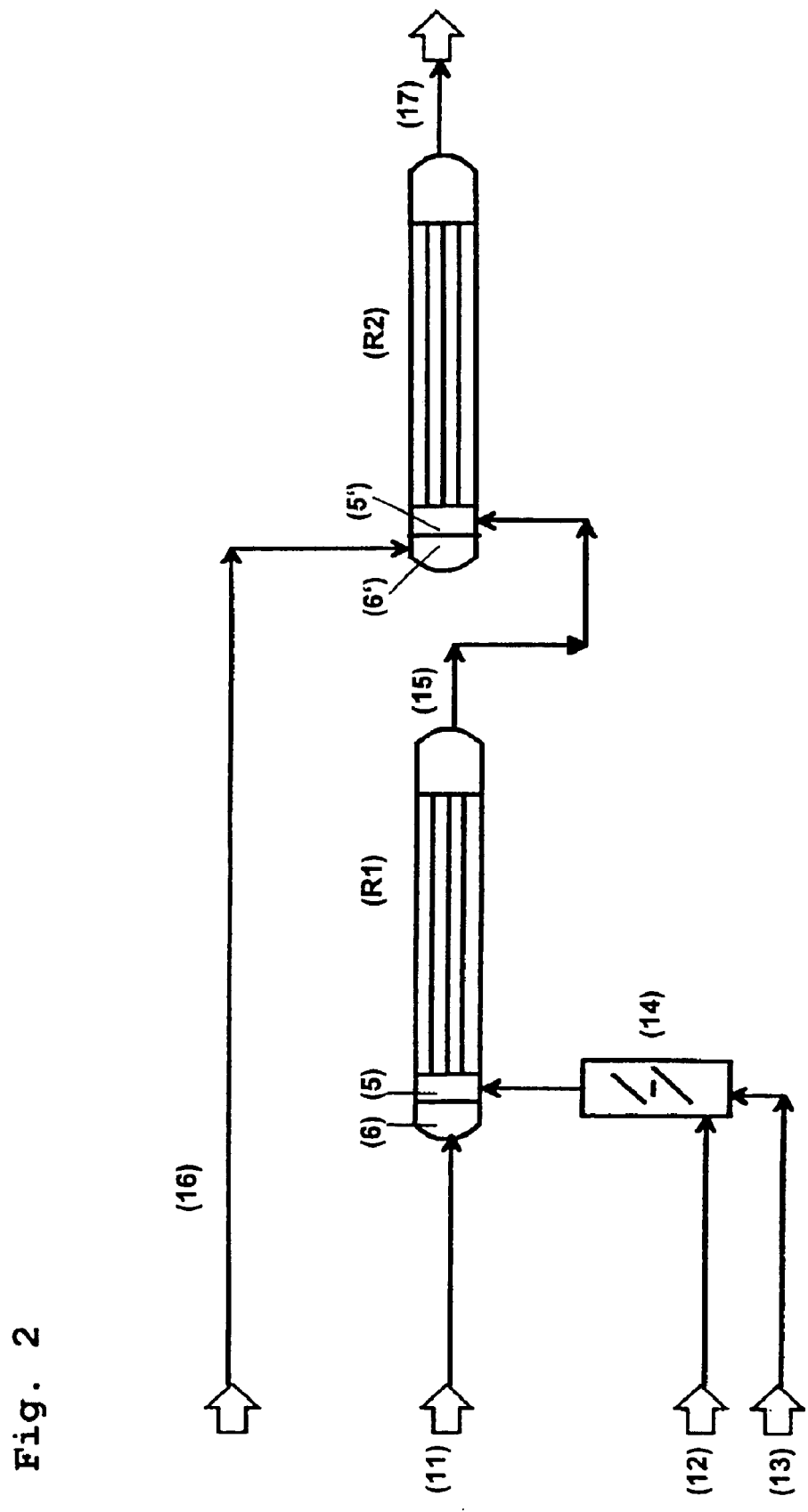

FIG. 2: Flow diagram of the continuous preparation of 2-bromo-2-nitro-1,3-propanediol.

FIG. 1 shows, in longitudinal section, part of a shell-and-tube reactor comprising a reaction tube (1) into whose end a second tube (2) having an outlet orifice (3) whose cross-sectional area is smaller than that of the reaction tube projects. The outer wall of the tube (2) together with the inner wall of the tube (1) forms a second outlet orifice (4). A static mixing element (7), for example a Sulzer SMX packing element, is located in the immediate vicinity of the outlet orifices (4) and (3). The tubes (1) and (2) are connected to chambers (5) and (6) which are not shown. Arrow (A) symbolizes the feed stream of aqueous formaldehyde and sodium hydroxide, while arrow (B) indicates the feed stream of nitromethane.

FIG. 1a schematically shows part of a shell-and-tube arrangement which comprises a plurality of the assemblies shown in FIG. 1. A plurality of reaction tubes (1) provided with mixing elements (7) go out from a plate (8). A plurality of tubes (2) project from a plate (9) into the tubes (1). Plate (9) together with plate (8) forms a chamber (5) which is provided with feed lines for the introduction of a reactant solution or a reactant. In turn, plate (9) together with the cap (10) forms a chamber (6) which is provided with feed lines for a reactant or a reactant solution.

FIG. 2 shows a flow diagram of the preparation of 2-bromo-2-nitro-1,3-propanediol according to the present invention. According to this flow diagram, a stream of nitromethane (11) is introduced via a chamber (6) into a shell-and-tube reactor R1. The shell-and-tube reactor R1 has a plurality of reaction tubes arranged as shown in FIG. 1 or FIG. 1a. An aqueous solution of sodium hydroxide (stream 12) and an aqueous formaldehyde solution (stream 13) are combined in a mixer (14) and fed via a chamber (5) into the reactor R1. The output from the reactor (15) is conveyed directly via a chamber (5) into the reactor R2. Reactor R2 has a reactor geometry comparable to that of the reactor R1 and likewise incorporates a plurality of the assemblies shown in FIG. 1 and FIG. 1a. Bromine (16) is fed via a chamber (6') into the reactor R2. The output (17) from reactor R2 is then passed to crystallization (not shown). Both the reactor R1 and the reactor R2 are connected to a cooling system (not shown).

I. Laboratory Experiment

Two coiled Teflon reaction tubes connected in series served as reactors. The first reaction tube had a length of 5000 mm and an internal diameter of 2 mm, corresponding to a reactor volume of about 15.7 ml. The second reaction tube had a length of 3000 mm and an internal diameter of likewise 2 mm, corresponding to a reactor volume of 9.4 ml. The first reaction tube had three inlets for liquids at one end. At its other end, it was connected via a connecting piece having an inlet for a liquid to the beginning of the second reaction tube. The free end of the second reaction tube led to a cooled receiver. Both the reaction tube (1) and the reaction tube (2) were cooled by means of cooling baths so that a maximum reactor temperature of +30° C. was not exceeded in reaction tube (1) and a maximum temperature of 20° C. was not exceeded in reactor (2). The receiver was cooled to −5° C. By means of automatic titrators (Metrohm Posimats), 3.43 ml/min of a 20% strength by weight aqueous formaldehyde solution, 0.54 ml/min of nitromethane and 1.8 ml/min of a 20% strength by weight aqueous sodium hydroxide solution were fed into the first reactor via the inlets provided. After about 50 ml had been fed in, 0.51 ml/min of bromine were fed in via the inlet in the connecting piece between the two reactors by means of a Metrohm Posimat. Virtually pure 2-bromo-2-nitro-1,3-propanediol crystallized out in the cooled receiver and was isolated by filtration. The yield of desired product, based on nitromethane used, was about 90%. This corresponds to a space-time yield of 4.3 kg/l$^{-1}$h$^{-1}$.

We claim:

1. A process for the continuous preparation of 2-bromo-2-nitro-1,3-propanediol, which comprises
    i) feeding nitromethane and one or two aqueous solutions comprising formaldehyde and alkali metal hydroxide continuously with mixing into a first, cooled reaction zone at molar ratios of formaldehyde to nitromethane of 1.9–2.2:1 and of alkali metal hydroxide to nitromethane of from 0.95:1 to 1.1:1,
    ii) taking the aqueous reaction mixture obtained in i) continuously from the first reaction zone and directly afterwards feeding this continuously together with bromine into at least one second, cooled reaction zone, and
    iii) isolating 2-bromo-2-nitro-1,3-propanediol from the aqueous reaction mixture obtained in ii).

2. A process as claimed in claim 1, wherein the residence time of the reactants in the first reaction zone is not more than 3 minutes.

3. A process as claimed in claim 1, wherein the first reaction zone is configured as a tube reactor or as a shell-and-tube reactor.

4. A process as claimed in claim 3, wherein nitromethane and the aqueous solution comprising formaldehyde and alkali metal hydroxide are fed via a nozzle having a first, central outlet and a second outlet arranged concentrically around the central outlet into the reaction tube via an apparatus suitable for mixing liquids.

5. A process as claimed in claim 1, wherein sodium hydroxide is used in step i).

6. A process as claimed in claim 1, wherein the reaction in the first reaction zone is carried out at below 40° C.

7. A process as claimed claim 1, wherein the second reaction zone is configured as a tube reactor or as a shell-and-tube reactor.

8. A process as claimed claim 1, wherein nitromethane and the aqueous solution(s) of formaldehyde and alkali metal hydroxide are fed via an apparatus suitable for mixing liquids into the first reaction zone.

9. A process as claimed in claim 8, wherein the aqueous reaction mixture obtained in i) and bromine are fed via an apparatus suitable for mixing liquids into the second reaction zone.

10. A process as claimed in claim 1, wherein the first and second apparatuses suitable for mixing liquids are each a static mixer.

11. A process as claimed claim 1, wherein the residence time of the reactants in the second reaction zone is less than 3 minutes.

12. A process as claimed in claim 1, wherein the reaction in the second reaction zone is carried out at below 30° C.

13. A process as claimed in claim 1, wherein the molar ratio of bromine to the nitromethane used in the first stage is in the range from 1.8:1 to 1.99:1.

14. A process as claimed claim 1, wherein the output from the second reaction zone is cooled to below 0° C. and the 2-bromo-2-nitro-1,3-propanediol which crystallizes out as a result is isolated.

* * * * *

UNITED STATES PATENT AND TRADEMARK OFFICE
CERTIFICATE OF CORRECTION

PATENT NO.   : 6,867,336 B2
DATED        : March 15, 2005
INVENTOR(S)  : Scherr et al.

It is certified that error appears in the above-identified patent and that said Letters Patent is hereby corrected as shown below:

Column 8,
Lines 41-44, delete and insert the following:
-- A process as claimed in claim 1, wherein the output from the second reaction zone is cooled to below 0°C and the 2-bromo-2-nitro-1,3-propanediol which crystallizes out as a result is isolated. --.

Signed and Sealed this

Seventh Day of February, 2006

JON W. DUDAS
*Director of the United States Patent and Trademark Office*